(12) United States Patent  
Dzwonczyk et al.

(10) Patent No.: US 7,657,309 B2  
(45) Date of Patent: Feb. 2, 2010

(54) MEASURING HUMAN HEART MUSCLE VIABILITY USING MYOCARDIAL ELECTRICAL IMPEDANCE

(75) Inventors: Roger R. Dzwonczyk, Columbus, OH (US); Carlos L. del Rio, Columbus, OH (US); Patrick I. McConnell, Columbus, OH (US); Michael B. Howie, Columbus, OH (US)

(73) Assignee: The Ohio State University, Columbus, OH (US)

( * ) Notice: Subject to any disclaimer, the term of this patent is extended or adjusted under 35 U.S.C. 154(b) by 375 days.

(21) Appl. No.: 10/555,470

(22) PCT Filed: May 28, 2004

(86) PCT No.: PCT/US2004/017224

§ 371 (c)(1),
(2), (4) Date: Nov. 2, 2005

(87) PCT Pub. No.: WO2004/105862

PCT Pub. Date: Dec. 9, 2004

(65) Prior Publication Data

US 2006/0235326 A1 Oct. 19, 2006

(51) Int. Cl.
*A61B 5/05* (2006.01)
(52) U.S. Cl. .................................................. 600/547
(58) Field of Classification Search .............. 600/506, 600/547
See application file for complete search history.

(56) References Cited

U.S. PATENT DOCUMENTS 5,454,377 A * 10/1995 Dzwonczyk et al. ........ 600/547
5,592,941 A * 1/1997 McMorrow ................. 600/443
5,767,117 A * 6/1998 Moskowitz .................. 514/219
6,731,978 B2 * 5/2004 Olson et al. ..................... 607/4

OTHER PUBLICATIONS

"An Evaluation of a New Two-Electrode Myocardial Electrical Impedance Monitor for Detecting Myocardial Ischemia", Anesth Analg 2001, 92:12-8.*

(Continued)

*Primary Examiner*—Max Hindenburg
*Assistant Examiner*—Michael C Stout
(74) *Attorney, Agent, or Firm*—Frank H. Foster; Kremblas, Foster, Phillips & Pollick (57) ABSTRACT

A method for detecting a quantitative measure of a physiologic state of a human myocardium or coronary artery. Implementations of the method detect the extent of change of myocardial electrical impedance from a mean baseline value to provide diagnosis of the extent of ischemia, stenosis, tissue rejection, and reperfusion and the effectiveness of cardioplegia and ischemia pre-conditioning as well as the general effectiveness of coronary bypass surgery as measured by post-operative reperfusion. Electrodes are attached to the myocardium, baseline measurements of the mean myocardial electrical impedance are stored and the variance of the myocardial electrical impedance and a baseline value of mean myocardial electrical impedance are computed from the baseline measurements and stored. Mean myocardial electrical impedance values are periodically measured between each electrode pair over an interval of time and stored. After the mean myocardial electrical impedance changes from the computed baseline value by at least the measured variance, the extent of change in the myocardial physiologic state is diagnosed as a continuous, smooth, function of the extent of change, or rate of change, of the periodically measured myocardial electrical impedance from the baseline value.

9 Claims, 6 Drawing Sheets

OTHER PUBLICATIONS

"Use of Myocardial Electrical Impedance to Assess the Efficacy of Preconditioning," CL del Rio et al. Computers in Cardiology 2002; 29:489-492.*

"Myocardial Electrical Impedance Response to Ischemia and Reperfusion in Humans," R Dzwonczyk et al. Computers in Cardiology 2002; 29:541-543.*

* cited by examiner

Fig. 1

| Patient ID | Age | Gender | Targeted Vessel | % Stenosis | Comments |
|---|---|---|---|---|---|
| 2 | 60 | M | LAD | 100 | |
| 3 | 73 | M | LAD | 90 | |
| 4 | 74 | M | LAD | 100 | |
| 5 | 58 | M | LAD | 95 | |
| 6 | 64 | F | LAD | 85 | |
| 7 | 59 | F | LAD | 75 | |
| 8 | 41 | M | LAD | 70 | |
| 9 | 53 | M | LAD + 1st Diagonal | 85 | 1st diagonal 85% stenosed |
| 10 | 62 | M | LAD | 70 | |
| 11 | 72 | F | LAD + 1st Diagonal | 95 | 1st diagonal 50% stenosed |
| 12 | 52 | F | RCA | 80 | |
| 14 | 49 | F | LAD | 85 | |
| 15 | 51 | F | LAD | 95 | |
| 16 | 54 | M | LAD | 70 | |
| 17 | 63 | M | LAD | 100 | |
| 18 | 49 | M | LAD | 80 | |
| 19 | 67 | F | LAD + 1st Diagonal | 75 | 1st diagonal 95% stenosed |
| 20 | 50 | M | LAD | 70 | |

| Parameter | P (n=7) | D (n=10) | H (n=7) |
|---|---|---|---|
| Baseline (W) *,† | 444.0±66.81 | 780.8±38.81 | 489.1±134.80 |
| Time to plateau (min) *,† | 4.7±1.15 | 46.3±12.93 | 4.1±1.91 |
| Normalized Plateau (%) ‡,* | 15.3±4.65 | 19.6±2.59 | 11.0±6.01 |

| MEI Parameter | ADO (n=5) | CTRL (n=5) |
|---|---|---|
| Peak MEI ($\zeta_{peak}$, %) | 21.08 ± 7.98 | 17.06 ± 5.01 |
| UT ($t_u$, min) | 2.76 ± 1.65 | 2.89 ± 0.95 |
| TC ($\tau$, min)(*) | 7.13 ± 1.03 | 4.56 ± 0.16 |

MEASURING HUMAN HEART MUSCLE VIABILITY USING MYOCARDIAL ELECTRICAL IMPEDANCE

BACKGROUND OF THE INVENTION

1. Field of the Invention

This invention relates generally to the use of myocardial electrical impedance (MEI) measurements for evaluating and diagnosing the physiologic and biochemical state of the human myocardial muscle, particularly during and after surgical procedures.

2. Description of the Related Art

Myocardial electrical impedance has been studied for over 125 years. Besides our work, no past research has involved human subjects. Myocardial electrical impedance holds promise in detecting and assessing various disease states of human heart tissue. Through animal and tissue experiments, MEI has been shown to correlate with the vitality of the myocardial tissue. Myocardial electrical impedance changes predictably with regional and global ischemia [1-3], edema [4], pathologic tissue ultrastructural changes (4), ATP depletion and lactate accumulation [1]. Methods and apparatus for measuring MEI are described in U.S. Pat. No. 5,454,377 which is herein incorporated by reference.

Recently researchers have demonstrated that MEI can reliably detect humoral rejection episodes following heart transplantation [5-7]. Cardiac tissue rejection results in global myocardial ischemia and other conditions that have previously been shown in animals to affect MEI. Currently, the condition of the transplanted cardiac tissue is monitored by routine histopathologic biopsies taken from the myocardium. The results from this procedure often take several days to obtain whereas MEI can be measured in a matter of seconds and can be measured more often, more safely and far less expensively than tissue biopsies. The benefit of using MEI rather than tissue biopsies is that tissue rejection could be diagnosed and treated earlier which will result in better preservation of the transplanted heart.

Myocardial electrical impedance has been used to compare myocardial preservation methods [3], measure the revivability of the heart [4] and to gauge tissue protection by beta-blockade from reversible ischemic damage [1]. It has been shown in animal experiments that MEI responds both to ischemia and reperfusion of the tissue [8]. Myocardial electrical impedance can therefore detect severe but reversible ischemic injury. The variable has been shown to assess the effects of cardioplegia and determine the need for and type of resuscitation following coronary artery bypass surgery. Myocardial electrical impedance can also assess the effects of tissue preconditioning, an important component of coronary artery bypass graft (CABG) surgery. Because MEI is anisotropic, where its absolute value depends on the orientation of the electrodes with the muscle fibers at any point in time, the parameter can also be used to determine the anatomic and physiologic orientation of the fibers. The physiologic orientation of the fibers changes with disease.

In the tradition of academic papers, we cite the following references:

[1] Ellenby M I, Small K W, Wells R M, et al. On-line detection of reversible myocardial ischemic injury by measurement of myocardial electrical impedance. Ann Thorac Surg 1987; 44:587-597.

[2] van Oosterom A, de Boer R W, van Dam Rth. Intramural resistivity of cardiac tissue. Med & Biol Eng & Comput 1979; 17:337-343.

[3] Garrido H, Sueiro J, Rivas J, et al. Bioelectrical tissue resistance during various methods of myocardial preservation. Ann Thorac Surg 1983; 36:143-151.

[4] Gebhard M M, Gersing E, C J Brockhoff, et al. Impedance spectroscopy: A method for surveillance of ischemia tolerance of the heart. Thorac Cardiovasc Surgeon 1987; 35:26-32.

[5] Mueller J, Warnecke H, Grauhan O, Nelson B, Cohnert T, Hetzer R. Electric impedance recording—A noninvasive method of rejection diagnosis. American Society of Extra-Corporeal Technology Proceedings 49-55.

[6] Grauhan O, Muller J, Knosalla C, Cohnert T, Siniawski H, Volk H D, Fietze E, Kupetz W, Hetzer R. Electric myocardial impedance registration in humoral rejection after heart transplantation. J Heart Lung Transplant 1996; 15:136-43.

[7] Pfitzmann R, Müller J, Grauhan O., et al. Intramyocardial Impedance Measurement for Diagnosis of Acute Cardiac Allograft Rejection. Ann Thorac Surgery 2000; 70:527-32.

[8] Howie M B, Dzwonczyk, McSweeney T D. An evaluation of a new two-electrode electrical impedance monitor for detecting myocardial ischemia. Anesth Analg 2001; 92:12-18.

[9] Dzwonczyk R, Liu A, Hartzler A. Method for measuring the myocardial electrical impedance spectrum. U.S. Pat. No. 5,454,377, Ser. No. 10/3/1995.

[10] Dzwonczyk R, del Rio C, Brown D A, Michler R E, Wolf R K, Howie M B. Myocardial electrical impedance responds to ischemia and reperfusion in humans. Computers in Cardiology 2002; 29:541-543.

[11] del Rio C L, Dzwonczyk R, Clymer B D, McSweeney T, Awad H, Czerwinski P, Howie M B. Use of Myocardial Electrical Impedance to Assess the Efficacy of Preconditioning. Comput Cardiol. 2002; 29:489-492.

[12] Flameng W J. Role of myocardial protection for coronary bypass grafting on the beating heart. Ann Thorac Surg 1997; 63:S12-22.

[13] Cinca J, Warren M, et al. Changes in myocardial electrical impedance induced by coronary artery occlusion in pigs with and without preconditioning. Circulation 1997; 96:3079-86.

[14] Tan H L, Mazón P, et al. Ischemic Preconditioning Delays Ischemia Induced Cellular Electrical Uncoupling in Rabbit Myocardium by Activation of ATP Sensitive Potassium Channels. Circ Res 1993; 27; 644:51.

[15] Kléber A, Riegger C B, et al. Electrical Uncoupling and Increase in Extracellular Resistance after Induction of Ischemia in Isolated, Arterially Perfused Rabbit Papillary Muscle. Circ Res 1987; 61:271-79.

[16] Yokota R, Fujiwara H, et al. Transient Adenosine Infusión Befote Ischemia and Reperfusion Protects Against Metabolic Damage in Pig Hearts. Am J Physiol 1995; 268:H1149-57.

[17] Yao Z, Gross G. A Comparison of Adenosine-Induced Cardioprotection and Ischemic Preconditioning in Dogs. Circulation 1994; 89:1229-36.

[18] Dzwonczyk R, et al. A New Apparatus and Method For Measuring The Myocardial Electrical Impedance Spectrum. Comput Cardiol 1992; 19:575-77.

[19] Skyschally A, Schulz R, Erbel R, Heusch G. Reduced coronary and inotropic reserves with coronary microembolization. Am J Physiol Heart Circ Physiol 2002; 282: H611-H614.

[20] Skyschally A, Erbel R, Heusch G. Coronary microembolization. Circ J 2003; 67:279-286.

[21] Grauhan L, Müller J, Knosalla C, Cohnert T, Siniawski H, Volk H D, Fietze E, Kupetz W, Hetzer R. Electric myocardial impedance registration in humoral rejection after heart transplantation. J Heart Lung Transplant 1996; 15:136-43.

[22] Pfitzmann R, Müller J, Grauhan O, Hetzer R. Intrmyocardial impedance measurements for diagnosis of acute cardiac allograft rejection. Ann Thorac Surg 2000; 70:527-32.

BRIEF SUMMARY OF THE INVENTION

Myocardial electrical impedance (MEI) is used in evaluating the vitality of myocardial tissue in humans and diagnosing various disease states of the human heart muscle. An array of electrodes is inserted into the myocardial tissue and MEI is measured between pairs of electrodes using any of a variety of electrical measurement and signal processing methods that are well known in the art. The condition of the myocardial tissue is determined from either the absolute value of any of the various components of the complex MEI, measured from one or more pairs of electrodes, such as the modulus, real part, imaginary part or phase angle, or combination thereof, measured at a particular frequency or combination of frequencies or from the change of any of the various components of the complex MEI or from the changes or rate of change of any of the various components, or combination thereof, of the complex MEI. In this manner, MEI can be used to detect physiologic and biochemical human myocardial tissue anomalies such as ischemia, reperfusion, rejection, adenosine triphosphate (ATP) depletion, lactate accumulation, electrolyte imbalances and/or ultrastructural tissues changes. MEI can also be used to determine and track changes in the anatomic and physiologic anisotropy of the heart tissue fibers. MEI can also be used to evaluate the effectiveness of various cardioplegia protocols and various preconditioning protocols, as well as the effectiveness of cardiothoracic surgery generally. MEI can also be used to detect tissue rejection following heart transplantation as well as the resolution of a rejection episode following treatment.

In order to obtain a quantitative measure of a physiologic state of a human myocardium or coronary artery from the electrodes, baseline measurements of the mean myocardial electrical impedance are recorded and the variance of the myocardial electrical impedance is computed from these measurements. A baseline value of mean myocardial electrical impedance is also computed from the baseline measurements. Mean myocardial electrical impedance values are measured over an interval of time and the data representing the impedance values as a function of time are stored. After the mean myocardial electrical impedance changes from the computed baseline value by at least the measured variance, the extent of change in the myocardial physiologic state is diagnosed as a continuous, smooth, function of the extent of change, or rate of change, of the periodically measured myocardial electrical impedance from the baseline value.

In describing the preferred embodiment of the invention which is illustrated in the drawings, specific terminology will be used for the sake of clarity. However, it is not intended that the invention be limited to the specific term so selected and it is to be understood that each specific term includes all technical equivalents which operate in a similar manner to accomplish a similar purpose.

DETAILED DESCRIPTION OF THE INVENTION

Figure 1:
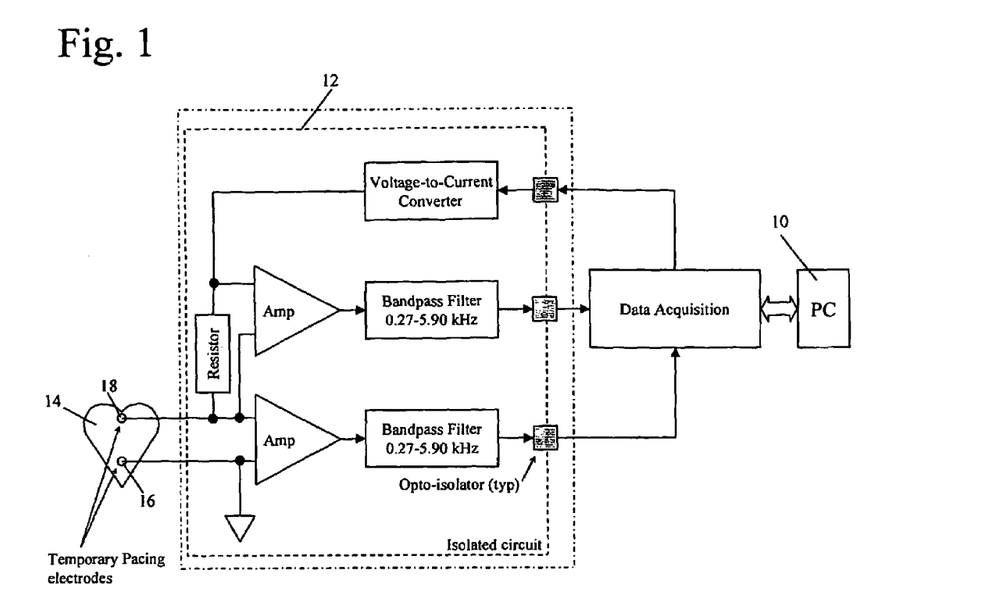
FIG. 1 is a block diagram of a myocardial impedance monitor that can be used for practicing the invention.

Referring to FIG. 1, the current MEI monitor is a modification of the original monitor described previously in U.S. Pat. No. 5,454,377. It consists of a laptop computer 10 that communicates with and controls custom analog circuitry 12 that, in turn, connects to the heart 14 via two temporary pacing electrodes 16 and 18 attached to the ischemic area of the myocardium 14. The personal laptop computer (PC) 10 generates the stimulus signal which is transformed into a 5 µA (100 µs) current pulse. The current pulse flows through a precision resistor and the myocardium 14 to ground. The current is measured across the resistor; the resultant voltage is measured across the myocardium. The current and voltage signals flow back to the PC for processing. The analog circuit is isolated.

An array of electrodes can be employed and the monitor can be connected to various groups of electrodes. The monitor impresses a zero-mean bipolar current signal on the myocardium and measures that current and the resulting voltage response. The current signal consists of a positive and negative 5 µA 100 µs impulses separated by 200 ms. Impedance is measured with the positive impulse and resultant voltage; the negative impulse serves to diminish the polarization effects at the electrode-tissue interface. The positive current and resulting voltage signals are amplified, band-pass filtered between 0.27-5.90 kHz and digitized, each into a 4,096 data-point 0.1862 s epoch, at 22.0 kHz. Ten impulse responses are obtained and averaged in the time domain to reduce noise in the current and voltage signals. The positive current impulse and associated voltage response are transformed into the frequency domain via fast Fourier transform processing. The current and voltage signals are smoothed with a 32-value moving average filter. Myocardial electrical impedance is calculated by dividing the frequency-domain voltage signal by the frequency-domain current signal at each frequency interval. The frequency domain resolution is 5.3711 Hz. The modulus of the MEI, one of the various components of the complex MEI, is evaluated from the real and imaginary components of the resulting impedance spectrum at each frequency interval and is reported as an average MEI modulus between 0.50 and 5.00 kHz. This average MEI value is linearized and calibrated with a second-order function. The parameters of this measurement methodology—for instance frequency range and sampling rate, among other parameters—can be varied while still producing a useful measurement of MEI. This technique for measuring MEI is one of several methods well known in the electrical measurement and signal processing art.

The modulus of the MEI is only one of several components of the complex MEI that can be evaluated to assess the viability of the myocardial tissue. Besides the modulus of the complex impedance, the real part, imaginary part and/or the phase angle, or combination thereof, at a particular frequency or combination of frequencies can be used to monitor the condition of the heart muscle. It is also understood that the absolute values of these components or the change or rate of change of these components, or combination thereof, at a particular frequency or combination of frequencies can be used to assess the viability of the tissue.

The following specific observations may be made regarding MEI and the myocardial tissue:

1. MEI increases with ischemia and decreases with reperfusion of the myocardium. This phenomenon has been the focus of much of our research. We have measured ischemia and reperfusion in several animal species. We are the only known group that has measured the phenomenon clinically in human patients;
2. The rate of increase of MEI during ischemia is species dependent. We are the only known group that has made this observation;
3. MEI detects and stratifies tissue rejection following heart transplantation;
4. MEI correlates to markers of myocardial metabolism during ischemia, namely ATP depletion and lactate accumulation as well as other biochemical ischemia markers;
5. MEI detects the effectiveness of cardioplesia, the protective methodologies used during on-pump coronary bypass graft and transplantation surgery;
6. MEI predicts the effectiveness of various methods of preconditioning, i.e. preparing the heart muscle for an ischemic event such as off-pump coronary artery bypass graft surgery. We have studied the differences between adenosine and ischemic preconditioning in pigs;
7. MEI detects ultrastructural (histologic) changes in the myocardial tissue;
8. MEI correlates to functional and ionic changes in the ischemic myocardium;
9. MEI indicates the anatomic and physiologic fiber alignment of the myocardium. Since physiologic fiber alignment changes in the failing heart, MEI may be an online indicator for chronic heart failure and recovery. This phenomenon is called electrical impedance anisotropy;
10. MEI measures the effectiveness of procedures such as coronary artery bypass graft (CABG) surgery, transmyocardial laser revascularization (TMLR) and other procedures that re-establish blood flow to the myocardium;
11. MEI acutely differentiates between normal, ischemic and infarcted myocardial tissue. MEI can therefore be used to delineate the region of the myocardium to be treated by, for instance, surgical ventricular restoration; MEI differentiates between normal, ischemic and infarcted myocardial tissue.

Although the method of the invention has various more specific implementations, generally the method detects, for diagnostic purposes, a quantitative measure of a physiologic state of a human myocardium or coronary artery. The method begins with attaching at least one electrode pair to the myocardium, although multiple pairs may also be used. A plurality of baseline measurements of the mean myocardial electrical impedance are then recorded, for example over a five or ten minute period. These baseline measurements are then used to compute the variance of the myocardial electrical impedance between the electrode pair or pairs. These baseline measurements are also used to compute a baseline value of mean myocardial electrical impedance. After the data are collected for determining the baseline value and the variance, mean myocardial electrical impedance values are periodically measured between the electrode pair over an interval of time. The data representing these periodically measured mean impedance values are stored in a computer as a function of time. This data is then displayed to a physician in some form, such as a graph on a computer monitor, printing on paper, as numerical data or modified by mathematical algorithms or for other graphical display.

After the mean myocardial electrical impedance values change from the computed baseline value by at least the measured variance, the extent of change in the myocardial physiologic state is then diagnosed as a continuous, smooth, function of the extent of change, or rate of change, of the periodically measured myocardial electrical impedance from the baseline value. The particular functional relationship between the change in the myocardial electrical impedance from the baseline value and the diagnosis it gives the physician is different for the different physiologic states being observed. But, in all cases, an increase in MEI is interpreted as signifying an increase in the pathophysiologic or diseased state of the heart muscle. Conversely, a decrease in MEI is interpreted as signifying a decrease in the pathophysiologic or diseased state of the muscle, or, in other words, an improvement in the vitality of the heart muscle. However, before describing the particular functional relationships, it would be helpful to discuss some mathematical terminology.

The invention is a diagnostic tool that, when applied in various alternative ways, provides the physician with a quantitative estimate of the extent of any of several physiologic states of the myocardium or coronary artery. The invention measures a first variable, the myocardial electrical impedance, and relates that to a second variable, a quantitative measure of a physiologic state of the myocardium. For example, when the invention is used to determine the pathophysiologic disease state, which is the extent of ischemia, the physician diagnoses the extent of the ischemia based upon the extent of the rise of the myocardial electrical impedance above the baseline value. The greater the extent of that rise, the more ischemic the myocardium. However, the change in the physiologic disease state is not necessarily directly proportional to the change in the myocardial electrical impedance because the term "directly proportional" implies a linear relationship. For example, a 20% increase in the myocardial electrical impedance above the baseline does not necessarily represent a 20% increase in ischemia. But, the greater the increase, the greater the ischemia. Similarly, when the method of the invention is used to obtain a quantitative estimate of reperfusion, the extent of the decline of the myocardial electrical impedance below the baseline indicates the extent of reperfusion. The more the decline, the more the reperfusion, but they are not necessarily directly proportional. As another example, when the method of the invention is used to determine the effectiveness of cardioplegia, the more the myocardial electrical impedance rises, the less effective the cardioplegia. As yet another example, when the method of the invention is used to determine myocardial tissue rejection following heart transplantation, the more the myocardial electrical impedance rises from baseline, the more serious is the episode of tissue rejection.

Thus, although the method of the invention measures the extent of changes in the myocardial electrical impedance and those measured changes indicate the extent of the change in a pathophysiologic disease state of the myocardium, in all cases, an increase in the myocardial electrical impedance represents an increase in the myocardial pathophysiologic disease state and the greater the increase in the impedance the greater the change in the myocardial pathophysiologic disease state. And conversely, a decrease in the myocardial electrical impedance represents a decrease in the myocardial pathophysiologic disease state and the greater the decrease in impedance, the greater the decrease in the pathophysiologic disease state.

At least one aspect of this invention, the effectiveness of preconditioning, relates to the rate of change of MEI over time. In this aspect of the invention, a more rapid rate of change of MEI indicates less effective preconditioning, whereas a less rapid rate of change of MEI indicates more effective preconditioning.

The science of mathematics has terminology describing these relationships between the measurement of the first variable, the myocardial electrical impedance, and the second variable, a quantitative measure of a physiologic state of the myocardium. The terms "continuous, smooth, increasing function", and "continuous, smooth, decreasing function" are mathematical terms that more precisely describe these relationships.

The term "continuous" means, in simple terms, that a plot of the functional relationship between two variables would have no discontinuities, that is, there is no broken jump. "Smooth" means that the derivative is continuous, that is, there is no sudden change in the slope of the curve. "Increasing" means that whenever the measured parameter increases, the quantitative measure of the physiologic state increases. "Decreasing" means that whenever the measured parameter increases, the quantitative measure of the physiologic disease state decreases. Summarized, "continuous, smooth, increasing function" means that the more the measured parameter increases, the more the quantitative measure of the physiologic disease state of the myocardium or its coronary artery increases and there are no sudden changes or discontinuities. "Continuous, smooth, decreasing function" means that the more the measured parameter increases, the more the quantitative measure of the physiologic disease state of the myocardium or its coronary artery decreases and there are no sudden changes or discontinuities.

Ischemia and Reperfusion of the Human Myocardium. To this point, all experiments with MEI have been carried out on nonhuman animals or in vitro on excised tissue samples. In this study we measured MEI clinically for the first time in human patients. Our patients were undergoing off-pump (moving heart) coronary artery bypass (OPCAB) surgery, a procedure that gave us the opportunity to study acute ischemia and reperfusion of the heart tissue and follow patients post operatively until their discharge from the hospital.

Figure 2:
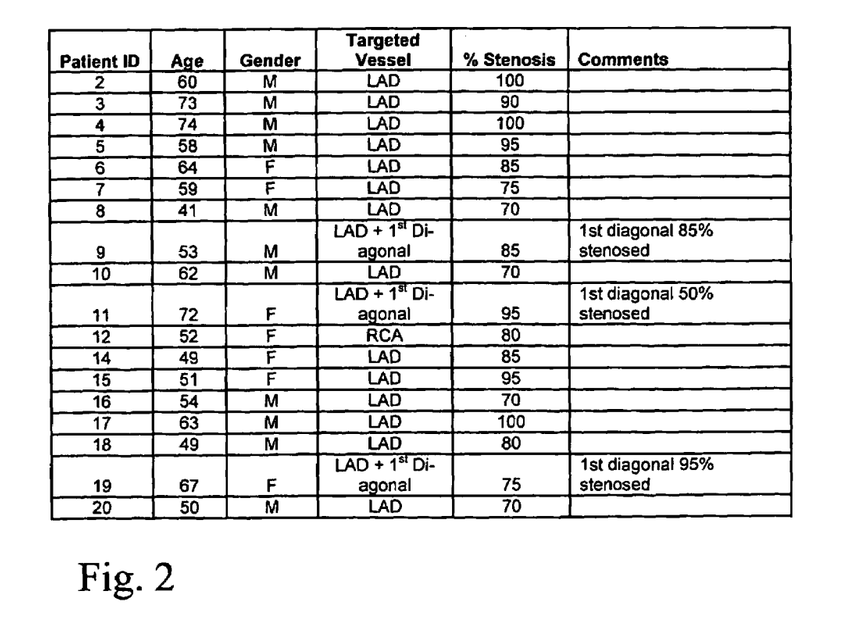
FIG. 2 is a table showing patient demographics.

Eighteen patients undergoing off-pump coronary artery bypass (OPCAB) surgery were studied (FIG. 2) (10). FIG. 2 shows patient demographics. LAD=left anterior descending coronary artery; RCA=right coronary artery. Patients 9, 11 and 19 also had the first diagonal branch of the LAD replaced. This branch feeds the myocardium in the measurement region. Patient 1 was eliminated from the study because of technical difficulties. Patient ID number 13 was not used.

The targeted surgery in this study involved the following steps;
 1. Isolate the left interior mammary artery (LIMA);
 2. Occlude the diseased coronary artery and LIMA;
 3. Anastomose the LIMA to the diseased artery distal to the stenosis;
 4. Reperfuse the ischemic myocardial tissue by un-occluding the diseased artery and LIMA.

The stenosis of the diseased artery of our patients ranges from 70%-100% as determined from cardiac catheterization. Myocardial electrical impedance was measured every 3 s during surgery and every 3 s for 5 min periods at 3, 6, 24 and 72 hrs postoperatively or until the measuring electrodes were removed from the patient's heart. For the postoperative measurements, the 5 min MEI data were averaged to generate one MEI reading per postoperative time interval per patient. Patients 9, 11 and 19 also had the first diagonal branch of the LAD replaced in addition to the LAD. Blood flowing in this branch feeds the myocardium in the MEI measurement region.

Figure 3:
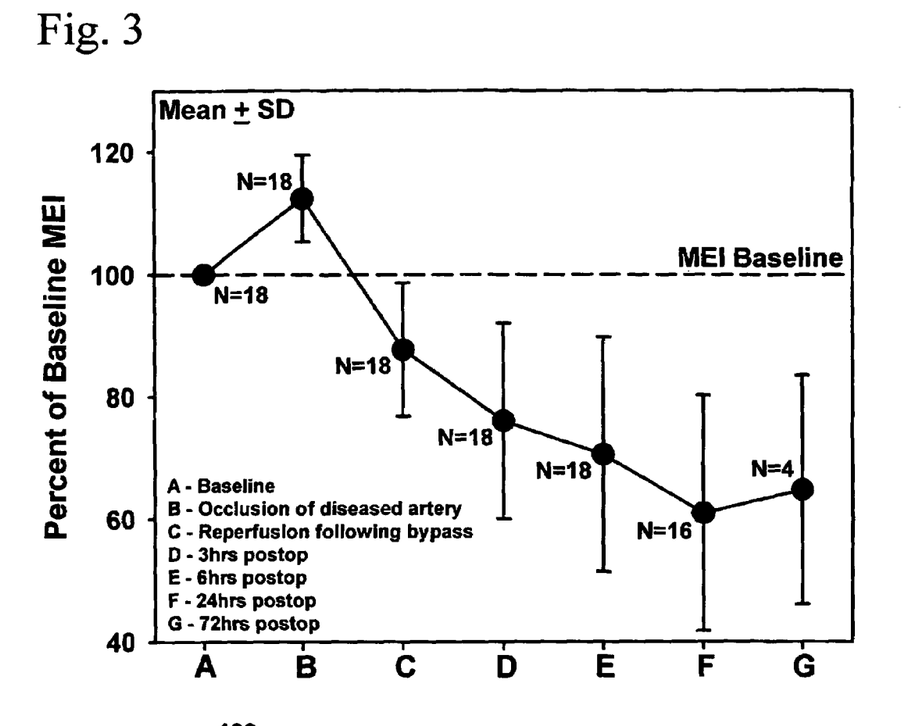
FIG. 3 is a graph showing percent changes in MEI prior to surgery, during surgery and postoperatively.

We report our data in percent, normalized per patient to baseline impedance measurements made following exposure of the heart but prior to beginning the targeted surgical procedure. Pearson product moment correlation was used to investigate the relationship between percent coronary artery stenosis and percent MEI increase at occlusion. FIG. 3 shows percent changes in MEI during surgery and postoperatively. The graph shows the effect of induced ischemia and surgical reperfusion on MEI. Data are presented as means±standard deviations. Each patient's data were normalized to their MEI value measured just prior to occluding the coronary artery targeted for bypass (baseline=100%).

Baseline MEI for our patients ranged from 173$\Omega$ to 769$\Omega$. The large range in absolute impedance was due not only to the disease state of the heart muscle but also to differences in electrode separation and electrode orientation with the myocardial fibers. For our patient population, MEI increased to 112.3%±7.1% of baseline on occlusion of the diseased artery and decreased to 87.7%±10.9% on reperfusion (FIG. 3, time point B and C, respectively). MEI continued to decrease during the measurement period (FIG. 3, time point D, E and F). The final measurement was 64.80%±18.7% of baseline (n=4) at 72 hrs (FIG. 3, time point G).

Figure 4:
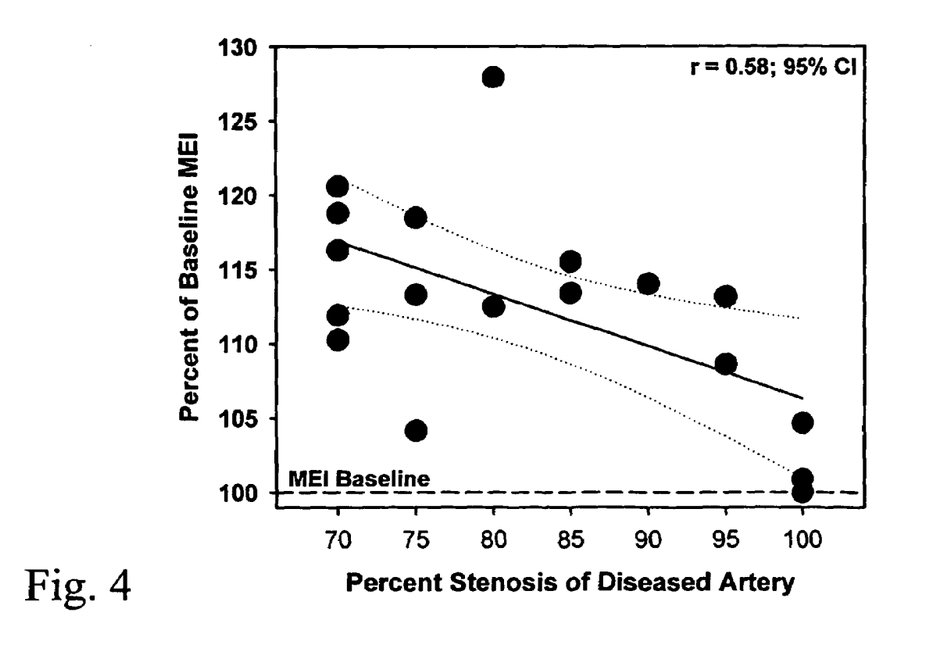
FIG. 4 is a graph showing the relationship between the percent stenosis of a diseased artery as a function of percent change in MEI following occlusion of that diseased artery prior to surgery.

FIG. 4 shows percent increase in MEI at occlusion (FIG. 3, time point B), prior to the targeted coronary artery surgery, as a function of the percent stenosis of the diseased artery. The graph shows the regression line of the data and its 95% confidence interval.

A significant relationship (r=0.58, p<0.05) existed between the percent increase in MEI on occlusion and the percent stenosis of the diseased artery taken from the cardiac catheterization report (FIG. 4).

Our patients experienced no adverse effects from the MEI measurements while anesthetized during surgery or awake postoperatively. There was no interference generated by our monitor that was detectable in the other physiologic monitors connected to the patient.

Changes in MEI can be used to measure the extent of pre-existing stenosis in a patient's coronary artery. At least one electrode pair is attached to the myocardium in the region of the myocardium perfused by the coronary artery. During surgery, but before occlusion of the artery, the usual above described baseline measurements are recorded and a mean myocardial electrical impedance, for use as a baseline, and the variance of the baseline measurements are computed. After the baseline measurements are made, the coronary artery is occluded proximally. The mean myocardial electrical impedance value between the electrodes is then periodically measuring over an interval of time and the measurement data is stored and displayed. After the mean myocardial electrical impedance rises above a value equal to the arithmetic sum of the mean baseline myocardial electrical impedance and the variance, the extent of stenosis pre-existing in the coronary artery is diagnosed as a continuous, smooth, decreasing function of the extent of rise of the mean myocardial electrical impedance above the baseline value. The more the value of MEI increases, the less restricted was the artery.

The human data illustrated in FIG. 4 can be approximated by the solid line of FIG. 4. That solid line can then be used to measure the extent of pre-existing stenosis in the coronary artery of other patients. That solid line can also be expressed as the equation:

% stenosis=−2.89×% MEI+410.044, where % stenosis is the percent pre-existing blockage in the coronary artery and % MEI is the increase of the mean myocardial electrical impedance above the baseline value expressed as a percent. Thus, the above equation is a particular continuous, smooth, decreasing function of % MEI derived from human data. Very precise numbers are used in the above expression in order to reflect the data we obtained. It should be understood that receipt of additional data may suggest some revision of those numbers to numbers which are substantially like those but depart from them but can be used to diagnose the percent of stenosis.

Species-specific Nature of MEI during Ischemia. Electrical impedance has been shown to reflect the myocardial response to ischemia [8], being correlated not only to functional abnormalities, but also to the underlying ionic and metabolic changes in the myocardium. However, the relevancy of its time course during ischemia is not clear. It has been found that MEI increases in a triphasic manner during ischemia: an early initial increase, a plateau phase, and thereafter, a rapid increase, thought to mark cellular uncoupling and irreversible damage.

We have observed similar MEI patterns in dogs and pigs [8, 11]. However, these species have well documented physiological differences, especially regarding collateral circulation pathways. Thus, a formal comparison between their responses to ischemia should highlight those MEI parameters that are able to differentiate between subjects with high (dogs) and low (pigs) probability of survival. To date, such a comparison is lacking. This study was designed to compare retrospectively the temporal behavior of MEI during acute occlusion of the LAD coronary artery in humans, with that of dogs and pigs.

MEI data was obtained from three previously presented studies performed at this laboratory with institutional approval [8, 11, 10], and divided into 3 groups (by specie): dogs (D), pigs (P), and humans (H). Human subjects studied had 70% to 80% LAD coronary artery stenosis.

Data was analyzed by a moving window technique, and within each window the best linear fit (least-squares sense) to the MEI data was calculated. The slope of the fit was used as an estimate of the MEI first derivative and its ischemic plateau value [11].

MEI baseline, time to plateau and normalized (by baseline) plateau value are presented as means with standard deviations (mean±sd). Mean cross-species differences were evaluated using a one-way ANOVA and the Student-Newman-Keuls post hoc test ($\alpha=0.05$).

Figure 5:
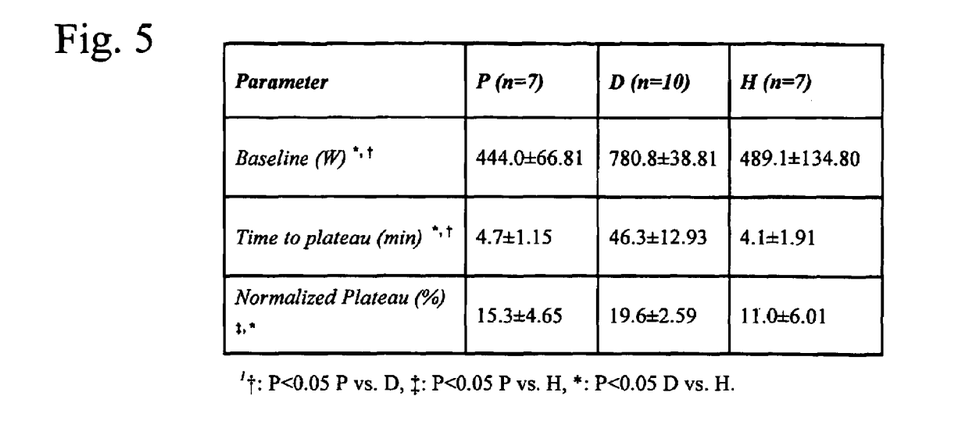
FIG. 5 is a table showing the MEI parameters in swine, canine and human myocardium.

As previously shown, after LAD coronary artery occlusion MEI increased significantly from baseline, reaching an ischemic plateau value subsequently. This holds true for all subjects and species studied. However, significant inter-species differences were observed (see FIG. 5), with the time to plateau showing the most remarkable ones. FIG. 5 shows the MEI parameters in swine (P), canine (D) and human (H) myocardium.

In dogs, MEI ischemic plateau was reached after 46.3±12.9 min of LAD occlusion. A significantly longer period when compared to that of pigs and humans. Similarly, non-ischemic baseline measurements from canine myocardium differed from those on swine and human myocardium.

No differences could be observed between swine and canine groups regarding their normalized ischemic plateau value, traditionally used to correlate MEI and ischemia. Contrastingly, humans had a lower ischemic plateau value (11.0±6.0%) than both animal species.

The extent and severity of myocardial ischemia has been shown to be dependant of its durations and of myocardial collateralization. Canines possess a well developed innate myocardium collateral system unlike humans or pigs, and have shown remarkably higher resistance to ischemia as reflected reduced rates of ATP depletion, lactate accumulation and smaller infarcts. Here, the MEI time course during ischemia has proven to be sensitive indicator of such superior ischemic resistance, and therefore could be a valuable predictive tool in the OPCAB setting.

The pathophysiologic disease state of ischemia in a portion of the myocardium can be measured by attaching the electrodes, taking and recording the above described baseline measurements and computing a mean myocardial electrical impedance, for use as a baseline, and the variance of the baseline measurements. The mean myocardial electrical impedance value between the electrodes is then periodically measured over an interval of time and the measurement data is stored and displayed. After the mean myocardial electrical impedance between the electrode pairs rises above a value equal to the arithmetic sum of the baseline myocardial electrical impedance and the variance, myocardial ischemia severity is diagnosed as a continuous, smooth, increasing function of the extent of the rise of the mean myocardial electrical impedance above the baseline value. The greater the increase in MEI, the more severe is the ischemia.

Similarly, the physiologic state of reperfusion can be measured by attaching the electrodes, taking and recording the above described baseline measurements and computing a mean myocardial electrical impedance, for use as a baseline, and the variance of the baseline measurements. The mean myocardial electrical impedance value between the electrodes is then periodically measuring over an interval of time and the measurement data is stored and displayed. After the mean myocardial electrical impedance between the electrode pairs declines below a value equal to the arithmetic difference of the baseline myocardial electrical impedance and the variance, the myocardial reperfusion level is diagnosed as a continuous, smooth increasing function of the extent of the decline of the mean myocardial electrical impedance below the baseline value. The more it declines, the better is the reperfusion. The extent of reperfusion as measured in this way can also be used as a diagnostic measure of the efficacy and level of success of coronary artery bypass surgery.

Using MEI to Assess the Efficacy of Preconditioning. Myocardial electrical impedance has been shown to change predictably with myocardial ischemia [1,4,8] and rejection [6], being sensitive not only to perfusion disturbances, but to metabolic and ultra-structural changes such as ATP depletion, lactate accumulation, edema and electrical cellular uncoupling. At this laboratory, it has been demonstrated (1) to increase immediately with occlusion of the left anterior descending coronary artery (LAD) reaching a plateau subsequently [8], and (2) to differentiate between drug-induced metabolic states. MEI, therefore, has potential value as an intra-operative monitoring and predictive tool, especially in beating heart myocardial revascularization procedures, where during the grafting process the heart muscle is forced to work in ischemic conditions and traditional ischemia monitoring techniques are ineffective.

In this setting, several preconditioning (PC) techniques attempt to protect the myocardium from an ischemic insult by raising its intrinsic anti-ischemic shields. Preconditioning, by brief periods of ischemia/reperfusion, referred as "ischemic preconditioning", has been found to increase myocardial tolerance, limit ATP wastage, attenuate myocardial acidosis and to reduce the rate of anaerobic glycolysis during prolonged ischemia (for review see [12]). On the other hand, these techniques have also been found to fail, and since there is no on-line, reliable and clinically feasible method to assess their efficacy, in practice, they are performed "blindly".

There is significant evidence that suggests MEI is a possible monitoring tool during preconditioning [13,14], given its ability to detect cellular uncoupling [15]. However, in such investigations, the early behaviour of MEI during ischemia (with or without PC), specifically before the onset of cellular uncoupling and cellular damage, has been neglected. Thus, the purpose of this study was to further investigate the value of MEI as a measure of preconditioning success.

The short-term effects of adenosine preconditioning on MEI were studied in a swine model of beating heart coronary artery revascularization. Adenosine infusion before acute ischemia has been shown to mimic the protective effects of ischemic preconditioning [16,17]. However, studies correlating this technique with MEI data are lacking.

With institutional approval, unconditioned juvenile farm pigs (25-30 kg) of either sex were anesthetized with Telazol (6 mg/kg) and Xylazine (2.2 mg/kg), placed on a respirator and instrumented with arterial and pulmonary artery (PA) catheters. Blood gases were sampled periodically and maintained within normal limits. Continuous monitoring included: Trans-esophageal echocardiogram (TEE), electrocardiogram (ECG), ST-segment, heart rate, pulse oximetry, temperature, cardiac output, arterial and PA pressures.

Sternotomy was performed, the heart exposed and suspended in a pericardial cradle. A portion of the LAD, distal to the first diagonal branch was isolated and a Robinson's vessel tie was loosely placed around the isolated portion of the artery. Two monopolar standard temporary pacing electrodes were placed in the region known to be rendered ischemic by the LAD occlusion, stitched 1 cm apart parallel to each other, and oriented perpendicular to the muscle fibers.

MEI was measured every second throughout the experiment in a fashion previously described [18] and demonstrated [8] and described above.

After instrumentation and 10 minutes of baseline recordings, the animals were randomly assigned to have either no preconditioning (CTRL, n=5) or adenosine preconditioning (ADO, n=5), receiving respectively, a 10 min infusion of placebo (0.9% normal saline) or adenosine (20 mg/kg) through the PA catheter distal port. Supportive Levophed (1 µg/kg) was co-infused with adenosine (ADO group) in order to maintain hemodynamic stability.

In both groups, infusion was followed by a washout period of 5 min, and an initial ischemia/reperfusion (IR) test period (10 min zero-flow ischemia/30 min reperfusion) performed. Upon completion of this insult, the animals were subjected to a second IR test of 30 min (each phase), mimicking a worse than average setting for coronary revascularization on the beating heart. In all cases, ischemia was induced by LAD occlusion, securing the Robinson's tie. A marker was placed in the MEI data after the LAD occlusion procedure was completed.

Figure 6:
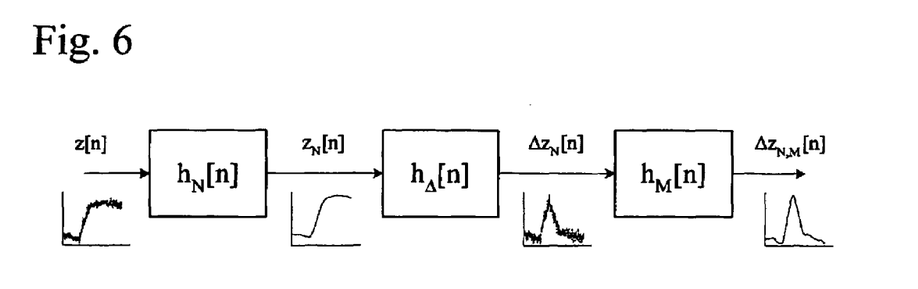
FIG. 6 is a block diagram illustrating the cascade of linear filters used to generate smooth signals representing the myocardial electrical impedance and its first derivate.

Myocardial electrical impedance recordings were assumed to be contaminated with zero mean white Gaussian noise. In order to mitigate its effects, the MEI signal was filtered using a moving average filter of length N=120 samples (2 min), $$z_N[n] = \sum_{i=0}^{N} h_N[i] \cdot z[n-i]$$

The weighting function was chosen to be rectangular, i.e.

$$h_K[n] = \begin{cases} \frac{1}{K+1} & 0 \leq n \leq K \\ 0 & \text{otherwise} \end{cases}$$

From the filtered MEI signal, a smooth approximation to the myocardial electrical impedance rate of change (first derivate) was computed using two linear filtering stages:

A two-point finite difference filter, i.e., $$\Delta z_N[n] = \sum_{i=0}^{1} h_\Delta[i] \cdot z_N[n-i] = z_N[n] - z_N[n-1]$$

A moving average filter of length M=60 (1 min) with weighting function $h_M[n]$ (as defined above), $$\Delta z_{N,M}[n] = \sum_{i=0}^{M} h_M[i] \cdot \Delta z_N[n-i]$$

FIG. 6 illustrates the cascade of linear filters used to generate smooth signals representing the myocardial electrical impedance ($z_N[n]$) and its first derivate ($\Delta z_{N,M}[n]$).

FIG. 6 summarizes and exemplifies the three filtering procedures described before. After filtering, the point of occlusion ($n_{occ}$) was selected as the sample (in a close neighborhood of the occlusion marker) where the smoothed MEI first derivate reached a local minimum (i.e., an MEI inflection point). In order to account for any differences in electrode spacing and placement, the filtered MEI data were normalized by the value at this time (baseline), i.e.

$$\zeta[n] = \frac{z_N[n] - z_N[n_{occ}]}{z_N[n_{occ}]}$$

Similarly, the sample where the smoothed MEI rate of change peaked ($n_{\Delta peak}$) was detected and used to normalize the filtered signal representing its first derivate, i.e., $$\Delta\zeta[n] = \frac{\Delta z_{N,M}[n]}{\Delta z_{N,M}[n_{\Delta peak}]}$$

For simplicity here, when referring to the normalized versions of the smoothed MEI and its derivate, the adjectives (normalized, smoothed, filtered, etc.) will be generally dropped, e.g., $\zeta[n]$ will be referred simply as MEI.

Two parameters commonly used in the literature to correlate myocardial electrical impedance with ischemia were extracted from the MEI data: "peak" change from baseline (i.e., MEI ischemic plateau value, $\zeta_{peak}$) [1,4,8], and cellular uncoupling time (UT, $t_u$). Electrical cellular uncoupling is usually associated with a 10% MEI change from baseline [6,14,15].

Additionally, considering that MEI's ischemic plateau may hold important information regarding physiological processes occurring during the early stages of ischemia, and that the initial fast rise in MEI may be due simply to vasculature compression after coronary flow elimination [14], a new third parameter was defined: time constant (TC, $\tau$). A TC was used to represent the time required by MEI to reach its ischemic plateau value ($\zeta_{peak}$) after its maximal rate of change was observed:

$$\tau = T \cdot (n_{peak} - n_{\Delta peak}),$$

where T=1 s is the MEI's sampling period, and $n_{peak}$ is the point (sample) where the MEI's rate of change ($\Delta\zeta[n]$) decreases below 3% of its peak value (observed at $n_{\Delta peak}$), in other words, $$\Delta\zeta[n_{peak}] \leq 0.03, \text{ and } n_{peak} > n_{\Delta peak}$$

Results are reported as means with standard deviations (mean±std. dev.) and parameter differences between groups were compared using two-sample student's t-test assuming unequal variances ($\alpha$=0.05).

Figure 7:
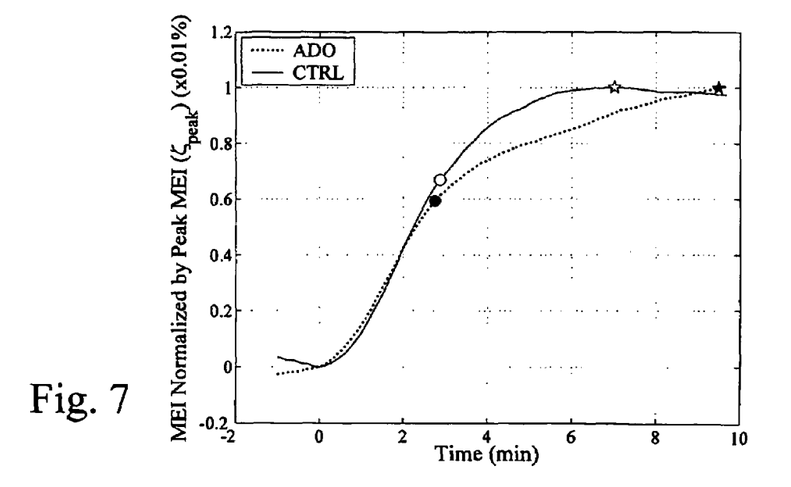
FIG. 7 is a graph showing the ensemble average of MEI normalized by the ischemic plateau value for control and adenosine-treated groups.

FIG. 7 shows the ensemble average of MEI ($\zeta[n]$) normalized by the ischemic plateau value ($\zeta_{peak}$, 5-point stars) for control (CTRL, n=5) and adenosine-treated (ADO, n=5) groups. Time zero (t=0 min) corresponds with the point of occlusion ($n_{occ}$), while circles mark cellular electrical uncoupling ($t_u$). Changes in the MEI signaled coronary perfusion disturbances produced by LAD occlusion. MEI increased immediately with induced ischemia, remaining elevated from its baseline value until reperfusion (FIG. 7), as expected.

However, the rate of change in MEI varied between groups and significant differences were observed. During ischemia, adenosine-treated animals (ADO) had a longer progression to ischemic MEI plateau, reaching such value in 9.49±1.29 min. While for animals in the control group (CRTL), stable MEI was observed in 7.02±0.33 min, i.e., 26% faster (P<0.05) as highlighted by FIG. 7.

As previously defined, a time constant (TC, $\tau$) represents the time required by MEI to reach ischemic plateau after its maximal rate of change has been observed. Thus, it was calculated that $\tau_{ADO}$=7.13±1.03 min in adenosine-treated animals, while $\tau_{CTRL}$=4.56±0.16 min in non-treated animals (P<0.05).

Figure 8:
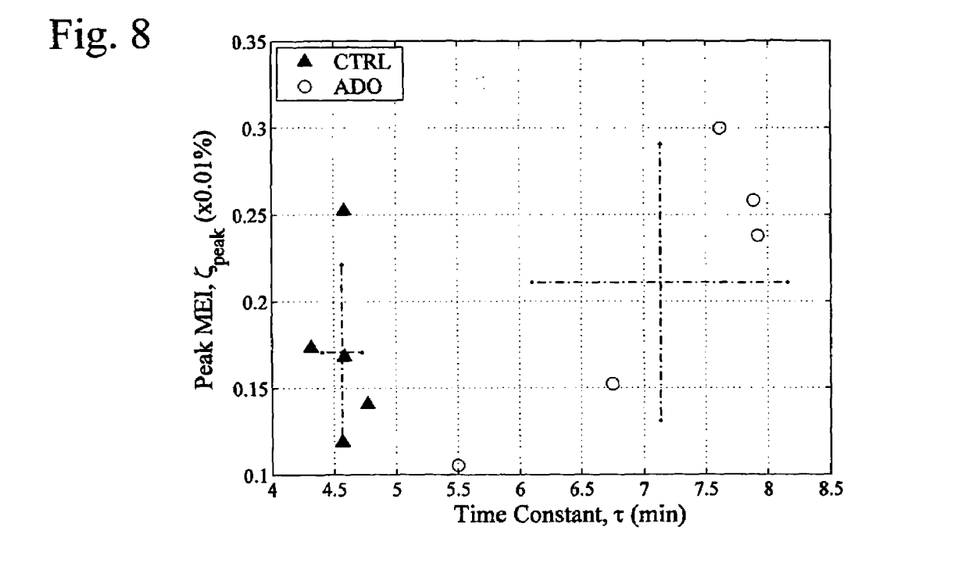
FIG. 8 is a graphical plot of data showing the relation between the ischemic plateau value and the time constant for control and adenosine-treated groups.
Figure 9:
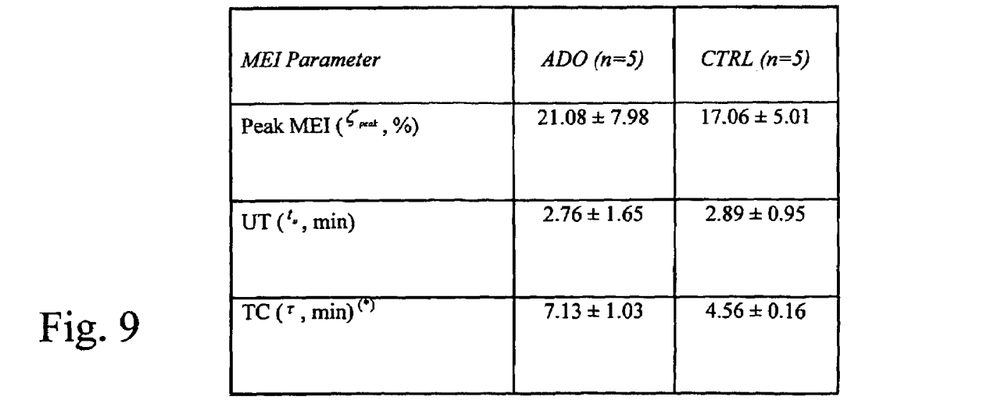
FIG. 9 is a table showing a set of MEI parameters extracted from in-vivo measurements.

FIG. 9 show a set of MEI parameters extracted from in-vivo measurements (*) indicates P<0.05). As it can be seen in FIG. 9, MEI's time constant ($\tau$) performed better than the MEI ischemic plateau value ($\zeta_{peak}$) and the cellular uncoupling time ($t_u$), since it is the only parameter of the three where significant differences were observed. For example, FIG. 8 compares the performance of MEI's time constant ($\tau$) against peak MEI percentage of change from baseline ($\zeta_{peak}$). (FIG. 8 shows the relation between the ischemic plateau value ($\zeta_{peak}$, ordinates) and the time constant ($\tau$, abscissas) for control (CTRL, filled triangles) and adenosine-treated (ADO, empty circles) groups. Notice the inter-group distance in the abscissa.

Additionally, all animals in the CTRL group developed ventricular fibrillation and died. Conversely, all of the adenosine-treated pigs (ADO group) survived and completed the experiment.

MEI, an electrical property of the heart muscle, was able to distinguish between control (CTRL) and adenosine-preconditioned (ADO) study animals. Such differentiation was achieved by studying the time required for MEI to reach a certain value relative to its ischemic plateau and to its maximal rate of change (i.e., a time constant).

In this study, a longer time constant was correlated with preconditioning success. Although further research is needed in order to correlate MEI with other properties of the preconditioning phenomenon, a meaningful definition of outcome-related MEI time constants might allow a quantitative early assessment not only of preconditioning success, but of several myocardial diseases.

Figure 10:
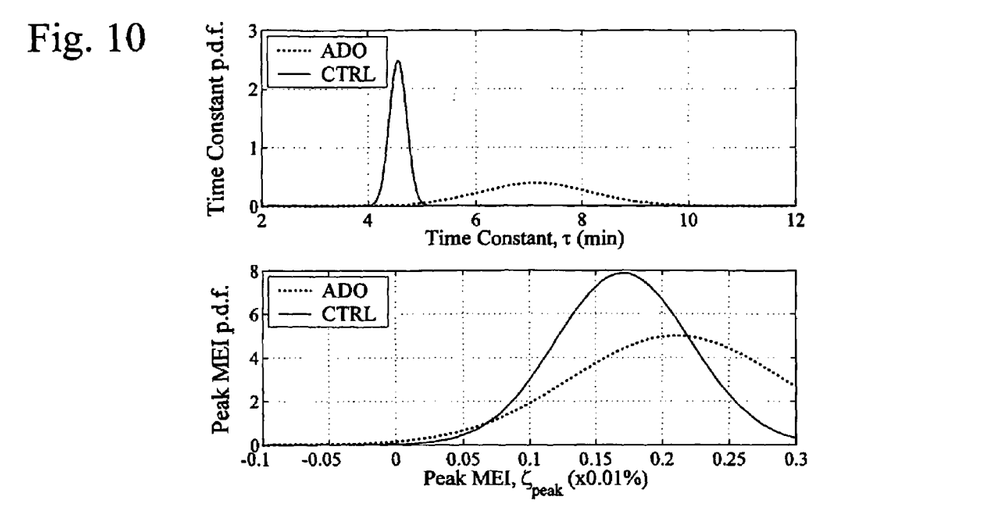
FIG. 10 is two graphs showing estimated normal distributions of peak MEI and the time constant for control and adenosine-treated groups.

Also, for the experimental conditions and sample size here presented, adenosine-treated animals displayed larger inter-subject variability in all the derived MEI parameters (see FIG. 9). This is further shown, by FIG. 10 where estimated normal distributions for peak MEI (ischemic plateau value, $\zeta_{peak}$) and MEI time constant ($\tau$) for control (CTRL, n=5) and adenosine-treated (ADO, n=5) groups were generated. A possible cause for this wider distribution is the short half-life of adenosine in plasma [16].

Further Data Regarding the Value of MEI in Assessing the Efficacy of Various Methods of Preconditioning. The myocardial electrical impedance (MEI) has been found to correlate with myocardial ischemia [8], ATP depletion and other diseased states of the myocardium. MEI, therefore, has potential value as a monitoring and predictive tool, especially during beating heart myocardial revascularization, where the heart muscle works in ischemic conditions during the grafting process. The current preconditioning (PC) techniques that exploit the intrinsic anti-ischemic defense mechanisms of the myocardium are performed blindly in clinical practice, since there is no reliable and clinically feasible method to assess their success. This experiment was performed to study the short-term effect of two common PC regimes, ischemic and adenosine-enhanced, on the MEI in a porcine model of beating heart coronary artery (CA) revascularization, in order to elucidate the value of MEI as a measure of PC success.

After institutional approval, 30 kg unconditioned juvenile farm pigs of either sex were anesthetized with Telazol (6 mg/kg) and Xylazine (2.2 mg/kg), placed on a respirator and instrumented with arterial and PA catheters. Anesthesia was maintained either with Desflurane or Isoflurane. Monitoring included: TEE, ST-segment, heart rate, pulse oximetry, temperature, cardiac output, blood and arterial pressures.

Sternotomy was performed and a portion of the left anterior descending CA (LAD) distal to the first diagonal branch was isolated. A Robinson's vessel tie was loosely placed around the isolated portion of the artery. Two mono-polar standard temporary pacing electrodes were placed in the region known to be rendered ischemic by the LAD occlusion, stitched 1 cm apart parallel to each other, and oriented perpendicular to the muscle fibers. From these leads, MEI was measured every 3 s throughout the experiment in a fashion previously described [8].

After 10 minutes of baseline recordings, the animals were assigned to have ischemic preconditioning (IPC) or Adenosine-enhanced IPC (IPCa), receiving a 10 min infusion of either Adenosine (20 mg/kg) (IPCa group) or placebo (IPC group) through the PA distal port. Supportive Levophed (1 ug/kg) was co-infused with Adenosine in order to maintain hemodynamic stability.

In both groups, the infusion was followed by a washout period of 5 min and IPC, consisting of 10 min zero-flow ischemia–30 min reperfusion. Upon completion of preconditioning, the animals were subjected to an ischemia/reperfusion (IR) test period of 30 min (each), mimicking a worse than average setting for CA revascularization on the beating heart. In all cases, ischemia was induced by LAD occlusion, securing the Robinson's tie.

Figure 11:
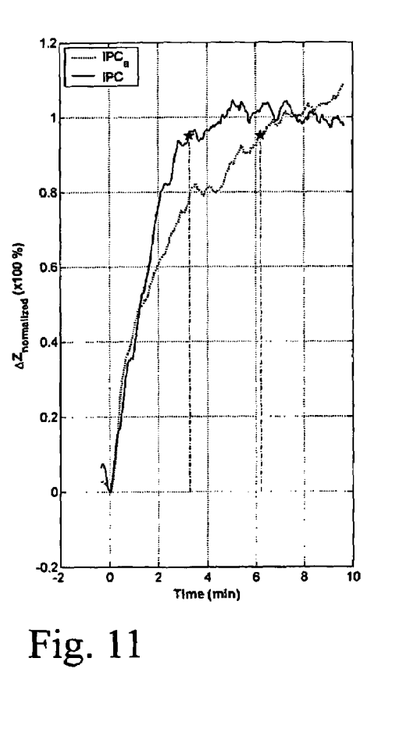
FIG. 11 is a graph of the normalized change in MEI as a function of time, during preconditioning, for test animals receiving ischemic preconditioning or Adenosine-enhanced ischemic preconditioning.
Figure 12:
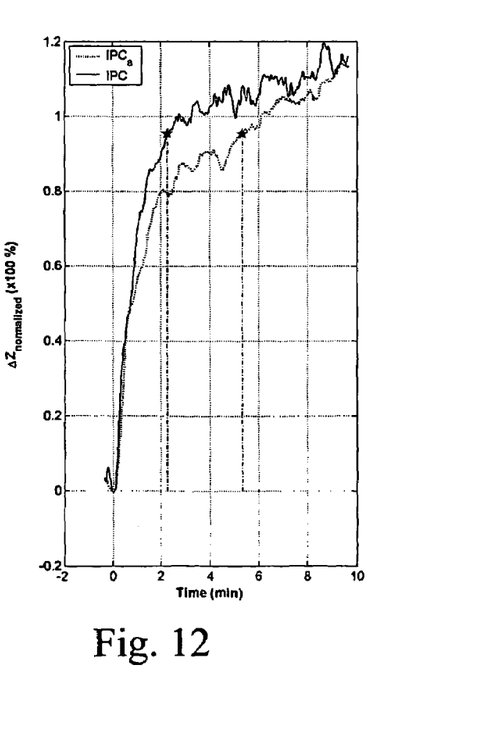
FIG. 12 is a graph of the normalized change in MEI as a function of time, during test occlusions, for the animals which were the subject of FIG. 11.

Changes in the MEI signaled coronary perfusion disturbances produced by LAD occlusion. MEI increased immediately with induced ischemia, remaining elevated from its baseline value until reperfusion, as expected [8]. However, the rate of change in MEI varied between groups and significant differences were observed. During preconditioning (FIG. 11), Adenosine treated animals (IPCa) had a longer progression to a stable MEI value, reaching such plateau in 7.8±1.6 min. In the control group (IPC), stable MEI was observed in 4.5±0.9 min, i.e. 42% faster. Similar differences were observed in the ischemic test period, after PC (FIG. 12), where MEI from IPC and IPCa pigs stabilized in 3.5±0.6 min and 5.7±1.3 min respectively. In FIGS. 11 and 12, corresponding to the preconditioning and test occlusions respectively, the time constant (TC) required by the MEI to reach 95% of its steady value is highlighted. Before preconditioning, TC=6.5 min in Adenosine treated animals, while TC=3.3 min in non-treated animals. After preconditioning, TC during test ischemia was shortened by more than 18%, to 5.3 and 2.3 min for IPCa and IPC groups respectively.

Additionally, all animals in the IPC group developed ventricular fibrillation and died during the IR test period. Conversely, 83% of the Adenosine treated pigs (IPCa group) survived. The MEI, an electrical property of the heart muscle, was able to distinguish between two common preconditioning schemes, IPC and IPCa. Such differentiation was achieved by studying the time required for MEI to reach one TC after induced ischemia. In this study, a longer TC was correlated with preconditioning success. Hence, and although further research is needed in order to correlate MEI with other properties of the preconditioning phenomenon, such as its graded nature, a meaningful definition of outcome-related MEI TC, might allow a quantitative early assessment of the preconditioning success.

Similarly, the effectiveness of ischemia preconditioning of the myocardium during coronary artery bypass graft surgery can be measured by attaching the electrodes, taking and recording the above described baseline measurements immediately prior to placing the heart on bypass and computing a mean myocardial electrical impedance, for use as a baseline, and the variance of the baseline measurements. The mean myocardial electrical impedance value between the electrodes is then periodically measured over an interval of time and the measurement data is stored and displayed. After the preconditioning and the beginning of the ischemic period of surgery, the rate of rise (ohms/minute) of the myocardial electrical impedance is calculated and displayed. The effectiveness of the ischemia preconditioning can then be diagnosed as a continuous, smooth, decreasing function of the extent of the rate of rise of the myocardial electrical impedance. The less the rise, the more effective was the preconditioning and conversely, the greater the rise, the less effective was the preconditioning.

Value of MEI in Assessing the Efficacy of Various Methods of Cardioplegia. The effectiveness of cardioplegia of the myocardium during on-pump coronary artery bypass graft surgery can be measured by attaching the electrodes, taking and recording the above described baseline measurements immediately prior to placing the heart on bypass and computing a mean myocardial electrical impedance, for use as a baseline, and the variance of the baseline measurements. After recording the baseline measurements, the myocardium is placed on bypass and a selected type of cardioplegia is applied. The mean myocardial electrical impedance value between the electrodes is then periodically measured over an interval of time and the measurement data is stored and displayed. After the mean myocardial electrical impedance between the electrode pairs rises above a value equal to the arithmetic sum of the baseline myocardial electrical impedance and the variance, the effectiveness of the cardioplegia is diagnosed as a continuous, smooth, decreasing function of the rise of the myocardial electrical impedance rises above the baseline value. The greater the rise in the MEI, the less effective was the cardioplegia.

MEI is a Reliable Intra-Operative Ischemia Monitor under β-Receptor Blockade and Stimulation. Traditional intra-operative ischemia monitoring has been performed by electrocardiographic techniques, such as ST-Segment analysis. However, and despite the development of heart rate compensating algorithms, its reliability under the effect of certain rhythm affecting drugs (e.g., β-blockers) has been a source of concern. This laboratory, has recently introduced and demonstrated the efficacy of a novel myocardial electrical impedance (MEI) monitor, designed for the intra-operative detection of myocardial ischemia [8]. MEI has been shown to correlate with myocardial ischemia, ATP depletion, and other diseased states of the myocardium. This study was designed to elucidate the reliability of MEI as a monitor of myocardial ischemia under three heart rate (HR) scenarios (normal, increased and depressed) induced by p-receptor stimulation/blockade in a canine model of beating heart coronary artery revascularization.

After institutional approval, 50 kg unconditioned male dogs were anesthetized with sodium thiamylal (10 mg/kg), intubated, and placed on a respirator. Anesthesia was maintained with a sodium thiamylal (4 mg/kg/hr) infusion and inhaled isoflurane. The heart was exposed through a median sternotomy and a portion of the left anterior descending coronary artery (LAD) distal to the second diagonal branch was isolated. A Robinson's vessel tie was loosely placed around the isolated portion of the coronary artery. A pair or standard temporary pacing leads were stitched approximately 1-cm apart, into the area of the myocardium expected to be rendered ischemic by occlusion of the LAD (i.e., by fastening of the vessel's tie). MEI was measured from these leads, using a device and technique developed at this laboratory and previously well described [8]. Monitoring included: electrocardiogram (ECG), HR, pulse oximetry (SpO2), temperature (T), cardiac output (CO), blood and arterial pressures (BP and PA, respectively).

Following 5 min of baseline measurements, the animals were randomly assigned to one of three study groups: control (CTRL), isoproterenol (ISO) and high-dose esmolol (E-H). Each group, received a 60 ml loading dose (ISO and CTRL: normal saline, E-H: esmolol 2 mg/kg) followed by continuous intravenous infusions. The animals assigned to the CTRL group received an infusion of normal saline (10 ml/min), while those in the ISO and E-H groups received isoproterenol (15 μg/min) and esmolol (1 mg/kg/min) respectively. After 15 min of continuous infusion, the animal were subjected to an ischemia/reperfusion insult, were acute myocardial ischemia was induced by occlusion of the LAD.

Figure 13:
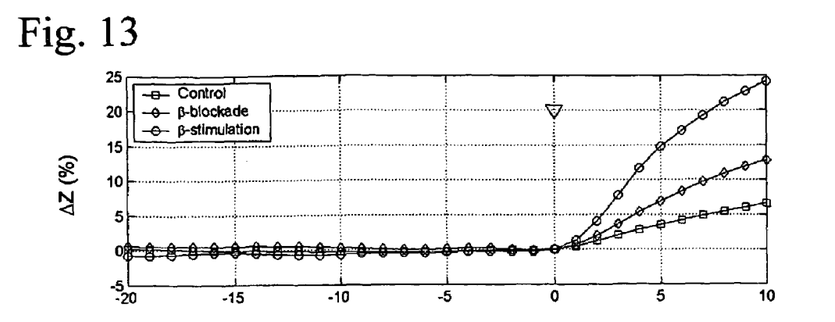
FIG. 13 is a graph illustrating changes in the MEI signaled coronary perfusion disturbances produced by LAD occlusion and reperfusion as a function of time.
Figure 14:
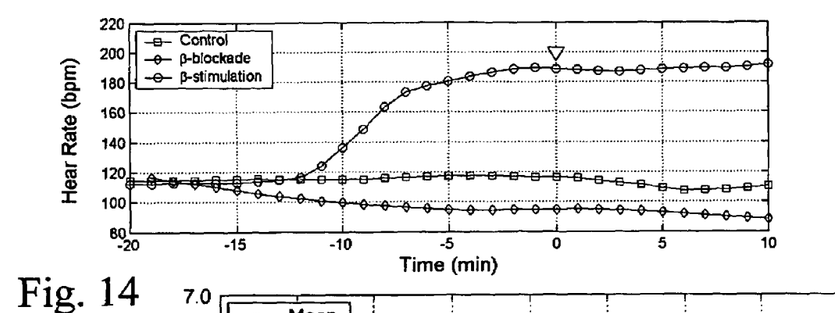
FIG. 14 is a graph illustrating heart rate of the test animals during the time interval of FIG. 13.

Changes in the MEI signaled coronary perfusion disturbances produced by LAD occlusion and reperfusion. In all animals, MEI increased immediately and significantly ($P<0.05$) only with induced ischemia, remaining elevated until reperfusion (FIG. 13). Such changes were not observed in the absence of induced ischemia, despite the fact that significant HR alterations were present in the animals assigned to the ISO and E-H groups (FIG. 14). Before occlusion, HR in the β-stimulated dogs (ISO), has increased $62.9\pm15\%$ ($P<0.05$) while in the β-blocked dogs (E-H) it has decreased $18\pm15\%$ ($P<0.1$).

Although MEI did not reflect HR changes in the normal non-ischemic myocardium, it was sensitive to the different metabolic rates induced by them during ischemia. While after 10 min of occlusion, the MEI rose only $6.6\pm2\%$ from its pre-occlusion value in the placebo group (CTRL); it increased $24\pm12\%$ and $13\pm5\%$ in the ISO and E-H groups respectively. MEI, an electrical property of the heart muscle, was not only able to reliably detect myocardial ischemia under rhythm changes induced by β-receptor stimulation and blockade, but also, to quantitative distinguish between the different metabolic states associated with them during ischemia. Such differentiation, achieved by studying MEI's rate of change, highlights the value of MEI as an intra-operative ischemia monitoring tool, especially in the setting of beating heart coronary artery revascularization, where the myocardium is forced to work in ischemic conditions during the grafting process, and a quantitative assessment of the ischemic insult is lacking.

Myocardial Electrical Impedance as a Monitor of Coronary Microembolization. Atherosclerotic plaque rupture, occurring either spontaneously or during coronary interventions, results in the release of thrombotic material into the coronary circulation, which may embolize the microvascular bed [19]. Such occlusive coronary thrombosis has been established as the decisive event in the pathogenesis of acute myocardial infarction (AMI), and sudden death [20]. The myocardial electrical impedance (MEI), a passive electrical property, has been found to correlate with myocardial ischemia [8], and ATP depletion. MEI, therefore, has potential as a coronary microembolization monitoring tool, especially during myocardial revascularization, where the risk of plaque rupture is increased. This experiment was designed in order to study the acute effects of selective left circumflex coronary artery (LCXa) microembolization (μ-embolization) on the MEI.

After institutional approval, adult Dorset sheep were chronically instrumented with posterolateral sonomicrometry crystals and two mono-polar pacing electrodes for segmental function and MEI measurements (respectively) in the LCXa distribution. The pacing wires were stitched 1 cm apart, parallel to each other, and oriented perpendicular to the muscle fibers. Subsequently, the animals were allowed to recover from surgery ($25.4\pm17.3$ days), and ten (N=10) selective LCXa μ-embolizations were performed. On anesthetized animals (telazol, etomidate, and isoflorane), 0.01-0.02 cc/Kg of 70-100 μm polystyrene beads were delivered (t=0 min) in the LCXa. MEI was measured every 3 s throughout the experiment in a fashion previously described [8]. Differences between pre-(baseline) and post-embolization MEI (normalized to baseline) and segmental shortening values were analyzed using a one-way ANOVA and Tukey post hoc tests ($\alpha=0.05$).

Figure 15:
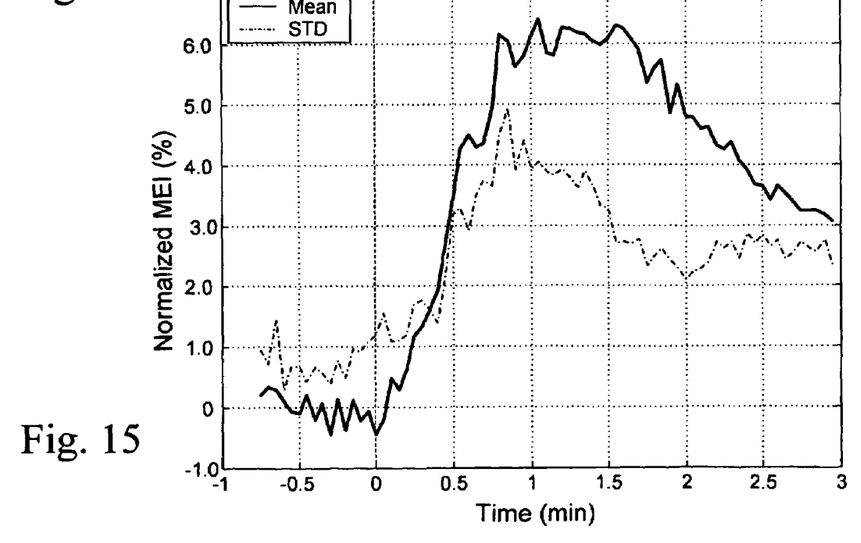
FIG. 15 is a graph illustrating changes in the myocardial electrical impedance following micro-embolization.

As expected, μ-embolization reduced segmental function in the LCXa distribution significantly. Systolic shortening decreased from $0.59\pm0.33$ mm at baseline (t=−0.25 min) to $-0.07\pm0.19$ mm (bulging, $P<0.05$) after injection (t=1.5 min). Similarly, immediately after μ-beads delivery, MEI increased significantly from baseline ($-0.44\pm0.38\%$, t=−0.25 min), reaching $5.32\pm2.30\%$ at t=1.5 min (see FIG. 15). In addition, cardiac Troponin I (cTNI) was measured 24 hr after embolization in a subset of procedures (M=5), and it was found to be significantly elevated (mean: 297.9 ng/mL, range: 119.7-548.0 ng/mL), corresponding with myocardial injury.

In this study, the myocardial electrical impedance (MEI), an electrical property of the heart muscle, measured by means of two standard temporary pacing wires, has been shown to indicate coronary microembolization precisely, but also to remain a viable monitor of ischemia in the chronic setting.

Myocardial Electrical Impedance Diagnoses Acute Cardiac Allograft Rejections. Acute cardiac allograft rejection is a global whole-organ process. Rejection is characterized by myocardial edema caused by capillary leakage [21]. It has been shown in animals [21, 22] that MEI is a sensitive and specific diagnostic measure of tissue rejection as compared with intramyocardial electrogram and the current gold standard indicator transvenous endomyocardial biopsy [21]. Further, it has been show that MEI increases with rejection, in proportion to the rejection severity. Therefore, MEI could be used to stratify acute cardiac allograft rejection into grades much like the International Society for Heart and Lung Transplantation (ISHLT) histologic grading of endocardiac biopsy. It is fully expected that these characteristics of MEI will be observed in rejection in humans.

The extent of myocardial tissue rejection following heart transplantation can be measured by attaching the electrodes, taking and recording the above described baseline measurements immediately following heart transplantation and computing a mean myocardial electrical impedance, for use as a baseline, and the variance of the baseline measurements. The mean myocardial electrical impedance value between the electrodes is then periodically measured over an interval of time and the measurement data is stored. After the mean myocardial electrical impedance between the electrode pair rises above a value equal to the arithmetic sum of the baseline myocardial electrical impedance and the variance, the myocardial tissue rejection severity is stratified as a continuous, smooth, increasing function of the rise of the myocardial electrical impedance above the baseline value. The greater the extent of the rise of MEI, the more severe is the tissue rejection.

While certain preferred embodiments of the present invention have been disclosed in detail, it is to be understood that various modifications may be adopted without departing from the spirit of the invention or scope of the following claims.

The invention claimed is:

1. A method for detecting a quantitative measure of a pathophysiologic state of a human myocardium or coronary artery of an individual, the method comprising:
   a) attaching at least one electrode pair to the myocardium;
   b) recording baseline measurements of the mean myocardial electrical impedance and computing the variance of the myocardial electrical impedance between each electrode pair;
   c) computing a baseline value of mean myocardial electrical impedance from the baseline measurements;
   d) periodically measuring mean myocardial electrical impedance values between each electrode pair over an interval of time and storing data representing the impedance values as a function of time; and
   e) after the mean myocardial electrical impedance changes from the computed baseline value by at least the measured variance, diagnosing the extent of change in the myocardial pathophysiologic state as a continuous, smooth, function of the extent of change, or rate of change, of the periodically measured myocardial electrical impedance from the baseline value.

2. A method in accordance with claim 1 wherein:
   a) the pathophysiologic state is the ischemia of a portion of the myocardium; and
   b) after the mean myocardial electrical impedance between the electrode pairs rises above a value equal to the arithmetic sum of the baseline myocardial electrical impedance and the variance, myocardial ischemia severity is diagnosed as a continuous, smooth, increasing function of the extent of the rise of the mean myocardial electrical impedance above the baseline value.

3. A method in accordance with claim 1 wherein:
   a) the pathophysiologic state is the extent of stenosis pre-existing in a coronary artery;
   b) each electrode pair is attached to the myocardium in the region of the myocardium perfused by the coronary artery;
   c) the coronary artery is occluded proximally after recording the baseline measurements; and
   d) after the mean myocardial electrical impedance between the electrode pair rises above a value equal to the arithmetic sum of the baseline myocardial electrical impedance and the variance, the extent of stenosis pre-existing in the coronary artery is diagnosed as a continuous, smooth, decreasing function of the extent of rise of the mean myocardial electrical impedance above the baseline value.

4. A method in accordance with claim 3 wherein the continuous, smooth, decreasing function is substantially:

$$\% \text{ stenosis} = -2.89 \times \% \text{ MEI} + 410.044,$$

wherein
% stenosis is the percent pre-existing blockage in the coronary artery and
% MEI is the increase of the mean myocardial electrical impedance above the baseline value expressed as a percent.

5. A method in accordance with claim 1 wherein:
   a) the state is the reperfusion of a portion of the myocardium; and
   b) after the mean myocardial electrical impedance between the electrode pairs declines below a value equal to the arithmetic difference of the baseline myocardial electrical impedance and the variance, the myocardial reperfusion level is diagnosed as a continuous, smooth increasing function of the extent of the decline of the mean myocardial electrical impedance below the baseline value.

6. A method in accordance with claim 5 whereby the efficacy and level of success of coronary artery bypass surgery is diagnosed as the extent of reperfusion.

7. A method in accordance with claim 1 wherein:
   a) the pathophysiologic state is myocardial tissue rejection following heart transplantation; and
   b) after the mean myocardial electrical impedance between the electrode pair rises above a value equal to the arithmetic sum of the baseline myocardial electrical impedance and the variance, the myocardial tissue rejection severity is stratified as a continuous, smooth, increasing function of the rise of the myocardial electrical impedance above the baseline value.

8. A method in accordance with claim 1 wherein:
   a) the state is the effectiveness of cardioplegia of the myocardium during on-pump coronary artery bypass graft surgery;
   b) the method further comprises, after recording the baseline measurements, placing the myocardium on bypass and applying a selected type of cardioplegia;
   c) after the mean myocardial electrical impedance between the electrode pairs rises above a value equal to the arithmetic sum of the baseline myocardial electrical impedance and the variance, the effectiveness of the cardioplegia is diagnosed as an inverse, continuous, smooth, increasing function of the rise of the myocardial electrical impedance rises above the baseline value.

9. A method in accordance with claim 1 wherein:
   a) the state is the effectiveness of ischemia preconditioning of the myocardium during coronary artery bypass graft surgery;
   b) the baseline measurements are recorded immediately prior to placing the heart on bypass;
   c) the method further comprises, after preconditioning and the beginning of the ischemic period of surgery, calculating the rate of rise (ohms/minute) of the myocardial electrical impedance; and
   d) the diagnosing step more particularly comprises diagnosing the effectiveness of the ischemia preconditioning as an inverse, continuous, smooth, increasing function of the extent of the rate of rise of the myocardial electrical impedance.

* * * * *

UNITED STATES PATENT AND TRADEMARK OFFICE
CERTIFICATE OF CORRECTION

PATENT NO. : 7,657,309 B2  Page 1 of 1
APPLICATION NO. : 10/555470
DATED : February 2, 2010
INVENTOR(S) : Dzwonczyk et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 370 days.

Signed and Sealed this

Thirtieth Day of November, 2010

David J. Kappos
*Director of the United States Patent and Trademark Office*